(12) United States Patent
Marx et al.

(10) Patent No.: US 6,306,644 B1
(45) Date of Patent: Oct. 23, 2001

(54) DEVICE FOR CULTIVATING DIFFERENT MAMMAL CELLS AT THE SAME TIME

(76) Inventors: Uwe Marx, Fercher Strasse 26, D-1152 Berlin; Gert Hausdorf, Rudolf-Seifert-Strasse 42, D-1156 Berlin, both of (DE)

( * ) Notice: Subject to any disclaimer, the term of this patent is extended or adjusted under 35 U.S.C. 154(b) by 0 days.

(21) Appl. No.: 09/803,048

(22) Filed: Mar. 12, 2001

Related U.S. Application Data

(62) Division of application No. 09/080,358, filed on Feb. 6, 1997, now Pat. No. 6,255,106, which is a continuation of application No. 08/146,193, filed as application No. PCT/DE92/00390 on May 13, 1997, now abandoned.

(30) Foreign Application Priority Data

May 17, 1991 (DE) .................................................. 41 16 727

(51) Int. Cl.[7] .................................................. C12M 1/00
(52) U.S. Cl. ..................................... 435/294.1; 435/286.5; 435/286.7; 435/289.1; 435/291.4; 435/294.1; 435/297.1; 435/297.4; 435/297.5; 435/373; 435/400
(58) Field of Search .............................. 435/286.5, 286.7, 435/289.1, 291.4, 294.1, 297.1, 297.4, 297.5, 373, 400

(56) References Cited

U.S. PATENT DOCUMENTS

| 3,948,732 | 4/1976 | Haddad et al. . |
| 4,722,902 | 2/1988 | Harm et al. . |
| 4,978,618 | 12/1990 | Kalina . |
| 5,010,014 | 4/1991 | Gebhardt . |
| 5,149,649 | 9/1992 | Miyamori et al. . |
| 5,190,878 | 3/1993 | Wilhelm . |

FOREIGN PATENT DOCUMENTS

| 839 245 | 5/1952 | (DE) . |
| 2537537 | 3/1976 | (DE) . |
| 39 23 279 A1 | 1/1990 | (DE) . |
| 0 200 226 | 11/1986 | (EP) . |
| 0 224 734 | 6/1987 | (EP) . |
| 0 230 223 | 7/1987 | (EP) . |

OTHER PUBLICATIONS

The Fisher Catalog, 1993–1994, p. 1260.

Primary Examiner—Leon B. Lankford, Jr.
(74) Attorney, Agent, or Firm—Fulbright & Jaworski

(57) ABSTRACT

A process and device are disclosed for simultaneously cultivating different mammal cells, for separately obtaining different mammal cell products and for simulating organic interactions on the humoral plane. Essentially, the invention consists of arranging several culture vessels in a common supply circuit and or cultivating different mammal cells in separate vessels.

18 Claims, 2 Drawing Sheets

DEVICE FOR CULTIVATING DIFFERENT MAMMAL CELLS AT THE SAME TIME

This application is a division of Ser. No. 09/080,358, filed Feb. 6, 1997, now U.S. Pat. No. 6,255,106, which is a continuation of Ser. No. 08/146,193, filed Aug. 24, 1994, now abandoned, which is a national stage entry of PCT/DE92/00390 International Filing Date: May 13, 1997.

BACKGROUND OF THE INVENTION

The invention relates to a process and device for simultaneous cultivation of different mammalian cells, for separate recovery of mammalian cell products, and for modeling of organ interactions. The applications of the basic bioreactor of the invention are applied medical research as well as the pharmaceutical industry.

To be able to cultivate mammalian cells efficiently in vitro. the culture conditions must be matched to a large extent to the in vivo conditions. In addition to constant pH and constant tempering, among other things, an optimum nutrient supply, an appropriate oxygen supply, cell-to-cell contacts) uniform removal of metabolic products, and cell debris removal are decisive here. Culturing systems in which the extracapillary space of dialysis culture flasks (e.g., hollow fiber cartridges) is used as a culture space for the cells come closest to meeting these requirements. Such dialysis culture flasks has been described in widely differing variations (U.S. Pat. Nos. 4,220,725; 4,391,912; 4,647,539; DE-PS 2431 450).

Permanently growing cell lines and proliferating primary cells can approximately achieve tissue cell densities in such culture flasks because of good supply and removal; this ensures cell unions with a specific optimum microclimate. As a result, high concentrations of cell products (recombinant proteins, monoclonal antibodies, growth factors, i.a.,) can be reached in the culture space. These products can then be recovered from the cell cultures. The bioreactors based on these culture flasks are optimized for large-scale cultivation of one cell type in each case (permanent cell line, proliferating primary tissue, i.a.,). The operating principle of the dialysis culture flasks has made it possible to use them as organ replacements (artificial kidneys) in medicine. Another organ-modeling bioreactor is presented in e.g., U.S. Pat. No. 4,242,460 in the form of a pancreas model. Cell culture devices in which several such culture modules are integrated in a common supply cycle and in which the pore size of the membrane separating the supply cycle and the culture spaces is variable have not been described previously.

The object of the invention is to develop a process and a culture device by means of which, on the one hand, relevant products can be produced from different mammalian cells in a culture batch and, on the other hand, the biological influences of different mammalian cells (primary cells, tissue, i.a.,) on one another can be studied in terms of organ interactions on the humoral level.

Figure 1:
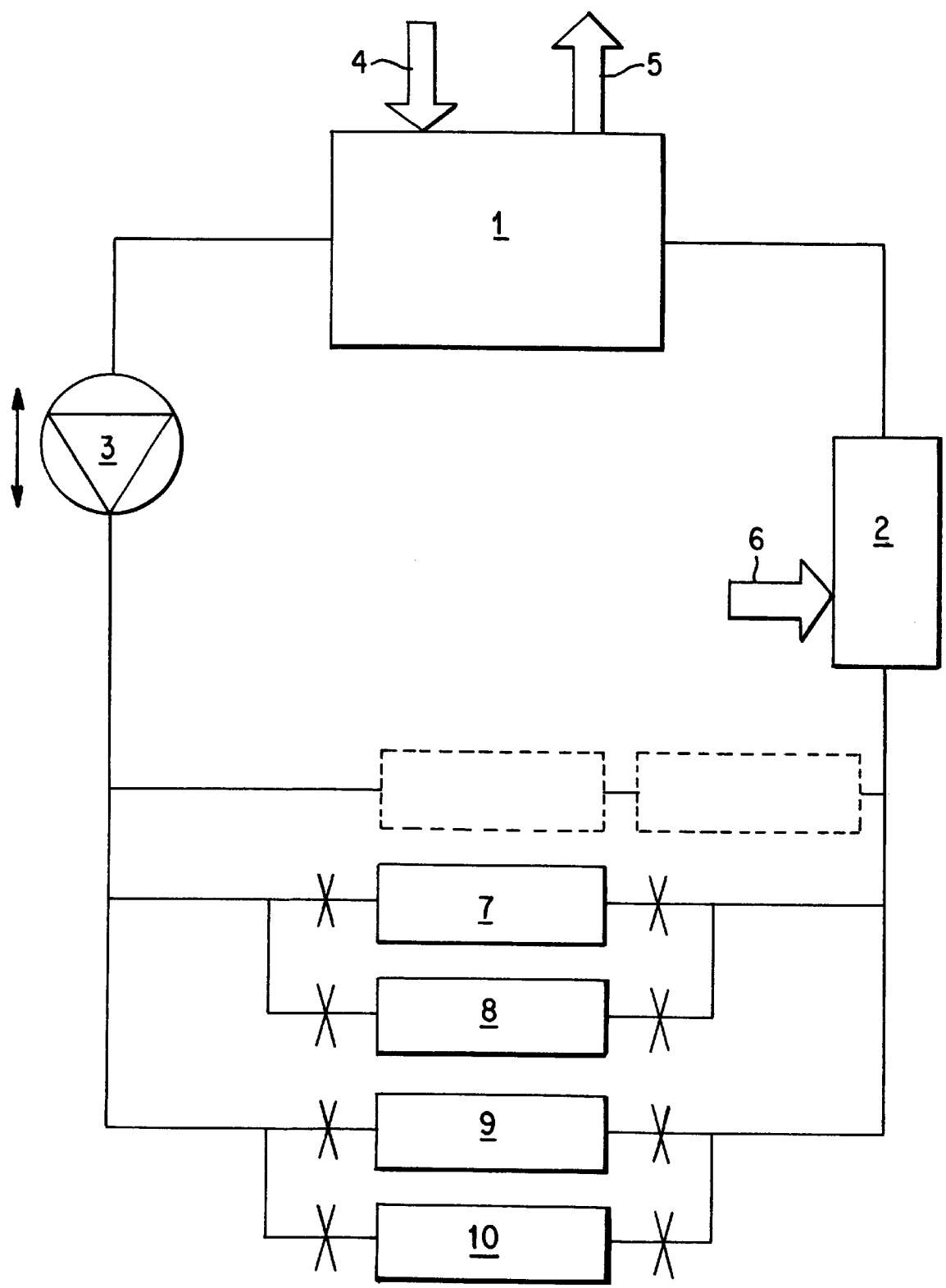
Figure 2:
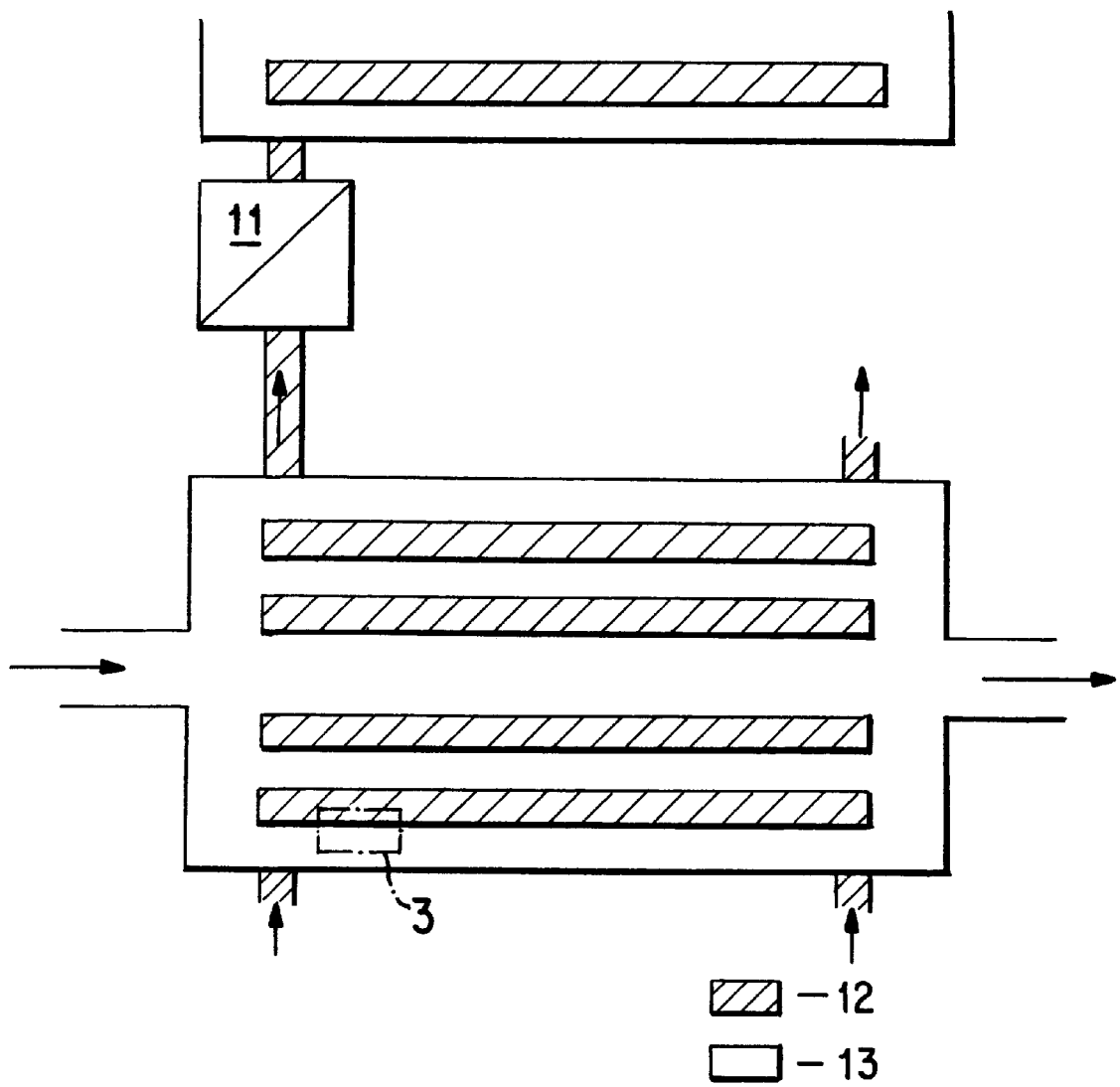

According to the invention, the object is achieved by integrating several separate culture flasks; e.g., in the form of modules, such as hollow fiber modules, into a common supply cycle (FIG. 1) and cultivating the various mammalian cells in each case in the culture flasks, e.g., in the extracapillary spaces of the hollow fiber modules—simultaneously, but separately from one another (FIG. 2).

According to the invention, the cell-populated space of each separate culture flask, which lies in the extracapillary spaces, e.g., the module, is separated from the supply cycle by a membrane or by membranes with variable pore sizes.

The products secreted, released or reacted by the individual cultures can be concentrated in the cell-populated culture spaces and/or recovered separately. Depending on their properties, according to the invention, they can also be transferred to the respective simultaneously cultivated flask and there cause defined biological effects (interaction factors). As a result, the individual culture flasks of the invention represent in vitro organ models which, in their influence on each other, duplicate organ interactions on the humoral level.

Another object of the invention relates to a device for simultaneous cultivation of different mammalian cells; another relates to using the device for the production of mammalian cell products and for medoling organ interactions on the humoral level.

Figure 3:
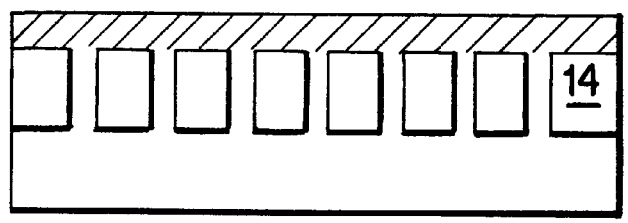

The supply cycle running through the intracapillary space of the modules consists of a tempered conditioning flask (1), an oxygenator (2) and a circulation pump (3). Metered fresh medium is fed (4) to the conditioning flask, and used medium is removed from it (5). By means of an oxygenator, the medium is supplied with oxygen (6). The pump ensures constant media circulation with unidirectional flow or periodically changing flow direction in the supply cycle. The individual modules (e.g., 7 and 9) are integrated into the circuit connected in series or in parallel and can be turned on or off separately by valves (X). A bypass module can be connected to every hollow fiber module provided for cultivation (e.g., 8 to 7 and 10 to 9). The cell-populated space of modules (12) is separated from supply cycle (13) by a cell-retaining membrane. In addition, it can be connected to cell-populated culture spaces of other modules via a microfiltration membrane (11), independently of the supply cycle. The pore size of fiber membrane (14) in the modules is varied, depending on the object, from less than 1000 daltons to more than 0.2 micrometer (FIG. 3). In the production of cell products in the cell-populated space, dialysis membranes with very small pore sizes, but in any case smaller than the cell products to be recovered, are used. In the modelling of an organ interactions on the humoral level, a permeable membrane is selected for important interaction factors (mediators, growth factors, metabolic products, and others).

Within the scope of this invention, "mammalian cells" are defined as primary mammalian cells, tissue structures of mammals, degenerated mammalian cells, permanently growing mammalian cell lines, or genetically modified mammalian cells or cell lines.

Within the scope of this invention, "culture flasks" are defined as all in vitro culture flasks in which the space populated by the mammalian cells is separated by a cell-retaining membrane from the supply cycle.

Within the scope of this invention, "bypass-modules" are defined as all flasks and structures which can simulate the biophysical parameters of the culture flask to be used by the respective bypass-module.

Within the scope of this invention, "cell products" are defined as all substances that are independently produced by the mammalian cells and can be used for medicine or research, e.g., antibodies, hormones, factors, enzymes, recombinant proteins, or other metabolic products.

Within the scope of this invention, "interaction factors" are defined as all substances, factors, components and other metabolic products—regardless of their type or origin—that are secreted, released, and reacted by the cultivated cells, in which connection the secretion, release or reaction can take place under the most widely varying conditions.

Within the scope of this invention, "organ interactions on the humoral level" are defined as all influences of mammalian cells on one another that are caused by the interaction factors in the individual culture flasks.

The solution of the invention makes it possible to cultivate different mammalian cells simultaneously, such as, e.g., primary cells, tissue structures and permanent cell lines, in culture flasks, e.g., hollow fiber modules of a bioreactor, in which case the different cell types are cultivated in each case in the extracapillary space of the module, by integrating the module into a common oxygenated supply cycle connected in parallel or in series. By varying the pore size of the membrane separating the culture spaces and the supply cycle, cell products in the extracapillary spaces can be retained separately, produced therein, and isolated therefrom. In addition, by appropriately modifying the pore size, interaction factors can be introduced into the supply cycle. As a result, the different mammalian cells can influence each other via the common supply cycle as a model of organ interactions on the humoral level.

With the solution of the invention, a universal culture system is made available to medical research and biotechnology in which, on the one hand, relevant products of various mammalian cells can be produced in a culture batch simultaneously, but separately from one another and, on the other hand, the biological influences of different mammalian cells on one another can be studied in terms of organ interactions on the humoral level.

EMBODIMENTS

Cell lines used: (A) human-mouse heterohybridoma
(B) murine hybridoma
Product: (A) human monoclonal IgG-antibodies
(B) murine monoclonal IgB-antibodies
Medium: Basal media mixture 1:1 IMEN and Ham's F12 for the supply cycle
Basal media mature (see above), as weU as 2.5% FCS and 2 g/l of human serum albumin for the cell culture spaces
Culture conditions: pH 7.0, $pO^2$—70% air saturation, temperature 37° C., media circulation speed—700 ml/min, Design:

Two DiaCap 1,2-dialysis hollow-fiber modules, connected in parallel, with an effective filter area of 1.2 $m^2$, were incorporated into the supply cycle of a CELL-PHARM-1-bioreactor. In the extracapillary spaces of the modules, $10^3$ cells each of hybridomas (A) and (B) were inoculated independently of one another. Cultivation took place over a period of 27 days. In 10 days, separate product harvests were taken from the extracapillary spaces. The samples were studied to ascertain the vitality of the extracted cells, antibody production and contamination with the other antibodies in each case. In addition, samples from the common supply cycle were periodically checked for the presence of antibodies. For antibody quantification, ELISA techniques and HPLC (high-pressure liquid chromatography) affinity chromatography were used.

Results:

There were no antibodies in the common supply cycle, nor were any cases of antibody cross-contamination detected in the cell-populated spaces.

This made it possible to recover the individual antibodies separately. Table 1 lists the most important test results.

TABLE 1

| | | Culture time (Days) | | | | | | | | | |
|---|---|---|---|---|---|---|---|---|---|---|---|
| | | 7 | 11 | 13 | 15 | 17 | 19 | 21 | 23 | 25 | 27 |
| MODULE (A) | hIgM | + | + | + | + | + | + | + | + | + | + |
| | mIgG | – | – | – | – | – | – | – | – | – | – |
| | vitality (%) | * | * | 53 | 69 | 83 | 90 | 78 | 93 | 87 | 77 |
| MODULE (B) | hIgM | – | – | – | – | – | – | – | – | – | – |
| | mIgG | + | + | + | + | + | + | + | + | + | + |
| | vitality (%) | * | * | 77 | 70 | 84 | 75 | 80 | 63 | 70 | 57 |
| cycle | hIgM | – | – | – | – | – | – | – | – | – | – |
| | mIgG | – | – | – | – | – | – | – | – | – | – |

Analyses of samples from the cell-populated spaces ((A)-heterohybridoma, (B)-murine hybridoma) and from the supply cycle checking for the presence of both antibodies and vitality of the extracted cells.
* = not determined,
+ = positive result,
– = negative result
hIgM = detection of human IgM
mIgG = specific detection of the murine antibody

REFERENCE SYMBOLS USED

FIG. 1: Diagram of the Culture System
1 Conditioning flask
2 oxygenator
3 circulation pump
4 supply of fresh medium
5 removal of used medium
6 oxygen supply
7 module
8 bypass-module
9 like 7
10 like 8
x valves
FIG. 2: Module Diagram with Microfiltration Membrane
11 Microfiltration membrane
12 cell-populated space
13 supply cycle
FIG. 3: Enlarged Detail of FIG. 2
14 Membrane (diagram)

What is claimed is:

1. A device for simultaneous cultivation of more than one different mammalian cell type, comprising:
   a conditioning flask adapted to receive fresh medium and from which used medium may be removed;
   an oxygenator;
   a pump capable of changing flow direction; and
   at least two culture flasks, each culture flask having one or more cell populated spaces;
   wherein said conditioning flask, said oxygenator, and said pump are linked together in a common supply cycle and said culture flasks are integrated into the common supply cycle either in parallel or in series.

2. The device of claim 1, wherein the cells in said cell populated spaces of each flask are capable of being recovered separately.

3. The device of claim 1, wherein said cell populated spaces have a cell-retaining membrane disposed between said spaces and said common supply cycle.

4. The device of claim 3, wherein said membrane has a pore size from about 1000 daltons to 0.2 micrometers.

5. The device of claim 1, wherein said culture flasks comprise hollow-fiber modules.

6. The device of claim 1, wherein said culture flasks can be separately turned on or off.

7. The device of claim 6, wherein said culture flasks are turned on or off by means of valves.

8. The device of claim 7, further comprising bi-pass flasks, said bi-pass flasks serving to keep the bio-physical parameters constant as individual flasks are turned on or off.

9. The device of claim 1, wherein said culture flasks are used for cultivating different mammalian cells.

10. The device of claim 1, wherein cells in one culture flask can influence cells in another culture flask.

11. The device of claim 1, wherein the cell populated space of at least one culture flask is surrounded by a cell-retaining membrane, wherein the pore size of said cell-retaining membrane is sized such that the cells in said cell populated space are retained while interaction factors are introduced into said supply cycle.

12. The device of claim 11, wherein said device is adapted to model organ interaction.

13. The device of claim 11, wherein said device is adapted to model organ interactions on the humoral level.

14. The device of claim 1, further comprising a connection between a first culture flask and a second culture flask independently of said supply cycle.

15. The device of claim 14, wherein said connection allows said first culture flask to influence said second culture flask.

16. The device of claim 14, wherein said connection allows interaction factors to pass from said first culture flask to said second culture flask.

17. The device of claim 14, further comprising a microfiltration membrane disposed in said connection.

18. The device of claim 17, wherein said microfiltration membrane is sized to allow predetermined interaction factors from one flask to pass to another flask.

* * * * *

UNITED STATES PATENT AND TRADEMARK OFFICE
CERTIFICATE OF CORRECTION

PATENT NO. : 6,306,644 B1
DATED : October 23, 2001
INVENTOR(S) : Uwe Marx et al.

Page 1 of 1

It is certified that error appears in the above-identified patent and that said Letters Patent is hereby corrected as shown below:

<u>Title page,</u>
Under "Related U.S. Application Data", change "May 13, 1997" to
-- May 13, 1992 --.

Signed and Sealed this

Twenty-eighth Day of May, 2002

*Attest:*

*Attesting Officer*

JAMES E. ROGAN
*Director of the United States Patent and Trademark Office*